(12) United States Patent
Stelcher

(10) Patent No.: US 6,896,741 B2
(45) Date of Patent: May 24, 2005

(54) TOOL FOR GATHERING MATERIALS INCLUDING PARTICLES AND HAIRS

(76) Inventor: William N. Stelcher, 729 Tyler Dr., Sarasota, FL (US) 34236

( * ) Notice: Subject to any disclaimer, the term of this patent is extended or adjusted under 35 U.S.C. 154(b) by 393 days.

(21) Appl. No.: 10/217,906

(22) Filed: Aug. 13, 2002

(65) Prior Publication Data

US 2004/0031504 A1 Feb. 19, 2004

(51) Int. Cl.$^7$ .............................................. A47L 25/00
(52) U.S. Cl. ................. 134/6; 15/104.001; 15/104.002; 15/209.1; 294/1.1; 436/174
(58) Field of Search ..................... 15/104.001, 104.002, 15/209.1, 210.1; 294/1.1; 134/6; 436/174

(56) References Cited

U.S. PATENT DOCUMENTS

| | | | |
|---|---|---|---|
| 3,409,928 A | * 11/1968 | Thurman .................... | 15/210.1 |
| 3,974,539 A | * 8/1976 | Barouh et al. .......... | 15/104.001 |
| 4,130,912 A | * 12/1978 | Sheppard et al. ........... | 15/210.1 |
| 4,637,089 A | * 1/1987 | Schwarz ....................... | 15/118 |
| 5,239,723 A | 8/1993 | Chen ...................... | 15/104.002 |
| 5,661,869 A | * 9/1997 | Grout ......................... | 15/209.1 |
| 5,765,887 A | 6/1998 | Weichman et al. .......... | 294/1.1 |
| 6,175,984 B1 | 1/2001 | Prime et al. ........... | 15/104.002 |

OTHER PUBLICATIONS

"Cleaning Stick", IBM Technical Disclosure Bulletin, vol. 30, No. 7, Dec. 1987.*

Dycem Contamination Control Price Sheet—Jan. 1, 2002.

* cited by examiner

Primary Examiner—Mark Spisich
(74) Attorney, Agent, or Firm—Schiff Hardin LLP

(57) ABSTRACT

A hand-held cleaning tool comprises a flexible elongated member having at one end a polymer cleaning element and a finger grip at the other end, the polymer being non-abrasive with inherent adhesion for small particles and hair, no aqueous solubility, non-corrosive, no particulate emission, and no separate chemical impregnation into the polymer.

17 Claims, 2 Drawing Sheets

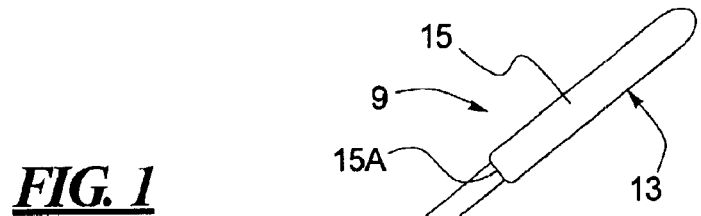
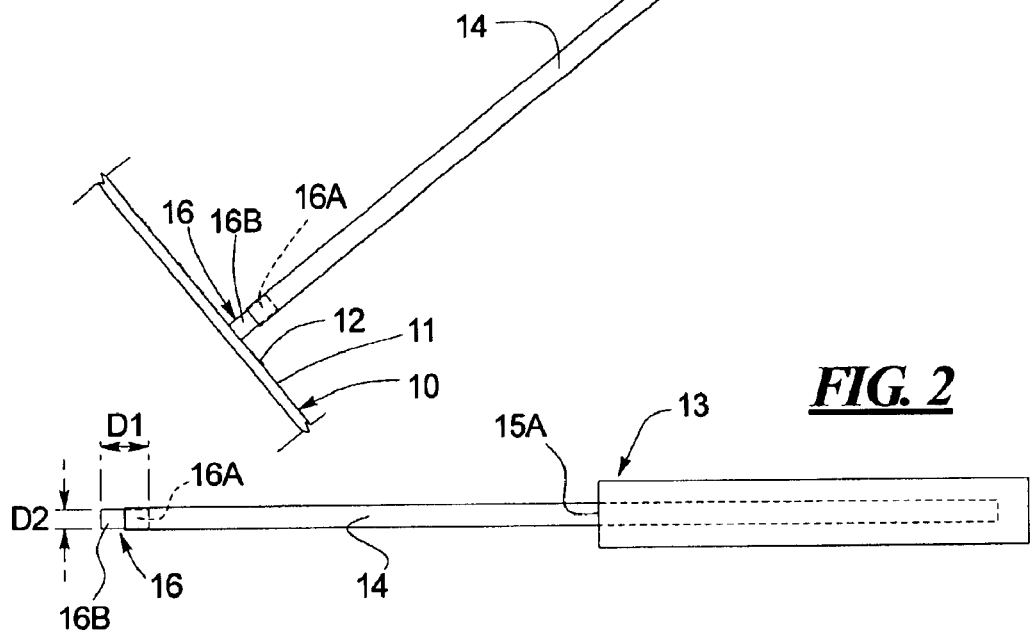
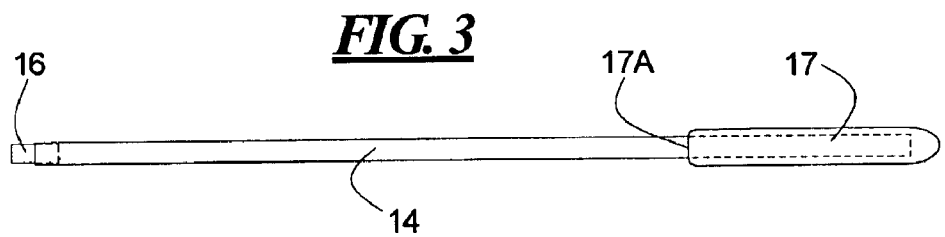
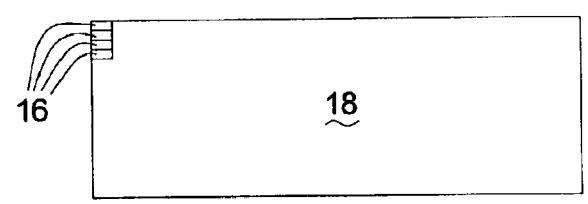
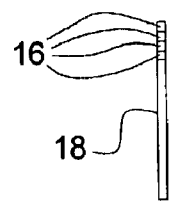

TOOL FOR GATHERING MATERIALS INCLUDING PARTICLES AND HAIRS

BACKGROUND OF THE INVENTION

In digital imagers, such as digital cameras, which employ charge coupled devices (CCDs), small dust particles or specs can accumulate on the face of the CCD. When a picture is taken with a camera, these minute particles show up in the image, thereby deteriorating the image. The minute particles are difficult to safely remove from the surface of CCDs, since the CCDs can be easily damaged. Not only the surface of CCDs are susceptible to accumulation of such small dust particles, but also films, camera mirrors, optics, and other sensitive surfaces can attract such small dust specs, thereby deteriorating the operating performance of those items or products. Removal of such minute particles is also difficult, since scratching or other types of damage may occur.

There is also a need in police work for gathering evidence such as small hairs or minute particles from objects without changing or damaging the surface characteristics of those objects from which the evidence is being collected.

SUMMARY OF THE INVENTION

It is an object of the invention to provide a cleaning tool, which removes or collects hair and/or fine particles such as small dust specs without damaging the surface from which the removal occurs.

According to the present invention, a long thin member is provided having a polymer material at an end of the member which captures particles and hair without leaving a residue on a surface from which the particles or hair are removed, but which does not damage the surface from which the particles or hair are removed. The polymer has a high adhesion surface that sticks to contaminant particles and/or hair with considerably more cohesive force then the surface from which the particles and/or hair are being collected. No residue is left on the contacted surface. The particles or hair can be removed from the polymer material by washing in water without diminishing its adhesive qualities. Furthermore, when the particles and/or hair are removed from delicate and sensitive surfaces, not only is no damage caused to the surface but there is also no additional contamination.

BRIEF DESCRIPTION OF THE DRAWINGS

FIG. 1 is a side view of a tool for gathering materials such as particles and hairs from a surface, but without damaging that surface;

FIG. 2 is a detailed side view of one embodiment of the tool of FIG. 1;

FIG. 3 is a second embodiment of the tool;

FIGS. 4a and 4b are a plan view and a side view respectively of a mat for one manufacturing process for creating a polymer tip on the tool.

DESCRIPTION OF THE PREFERRED EMBODIMENTS

Figure 5:
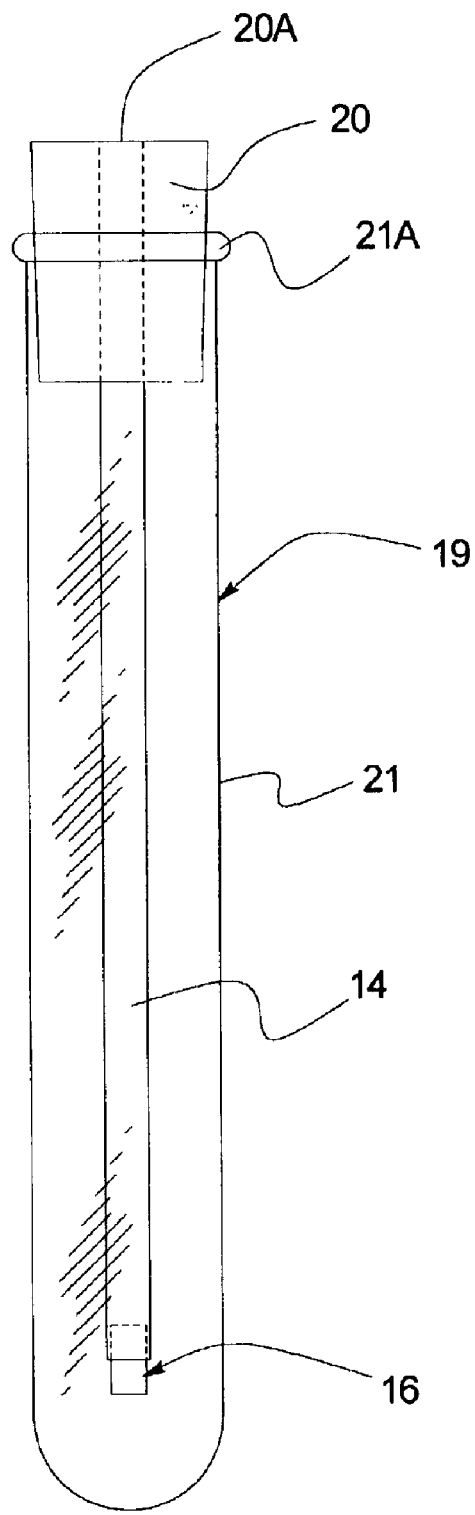
FIG. 5 is a side view of an embodiment wherein the tool is used for collection of evidentiary material in police work.

For the purposes of promoting an understanding of the principles of the invention, reference will now be made to the preferred embodiments illustrated in the drawings and specific language will be used to describe the same. It will nevertheless be understood that no limitation of the scope of the invention is thereby intended, such alterations and further modifications in the illustrated device, and/or method, and such further applications of the principles of the invention as illustrated therein being contemplated as would normally occur now or in the future to one skilled in the art to which the invention relates.

The tool for gathering materials including hairs and minute particles is shown in a side view at 9 in FIG. 1. Preferably, the tool is a hand tool easily manipulated by the fingers of the user. The tool has a handle 15 which receives an elongated member such as a hollow plastic tube 14 having an outside diameter from 1/16" to 1/2", and with CCD applications from about 1/8" or less.

On the end of the tube 14, a polymer cleaning element 16 is provided which is formed with a square cross-section having dimension D2 of 1/2" or less (FIG. 2) and a length D1 (FIG. 2) of about 1/2" or less. Approximately, one-half of the element 16 at 16a is forced into the end of the tube 14 with the portion 16b being exposed at the end of the tube 14 (FIG. 2). The force fit results from compression of the corners of the square cross-section.

During use, small minute particles 11 such as dust specs or the like, or alternatively hair fragments 12, can be removed from a surface 10 without damaging the surface 10.

One preferred use of the invention is for removing minute dust specs from delicate and sensitive surfaces such as the CCD array in a digital imager or camera without damaging the CCD surface. Also, the tool is useful on mirrors, lenses, UV windows, films, silicon wafers, and other hard to clean surfaces. Additionally, the tool is useful for gathering and preserving evidence in police work where the evidence in the form of small particles and/or hairs are adhered to a surface 10 which cannot be damaged during the gathering and recovery of the potential evidence.

As shown in FIGS. 2 and 3, the handle may be a large rubber handle such as shown at 13 having an aperture 15a receiving an end of the tube 14. Alternatively, as shown in FIG. 3, a thin plastic cap 17 serving as a handle receives at its inside aperture 17a the end of the tube 14.

The polymer-cleaning element 16 is preferably a polymer which is non-abrasive, non-corrosive (including no-outgassing), and which has inherent adhesion, no aqueous solubility, no particulate emission, and no separate chemical impregnation into the polymer. One form of such a polymer material, which can be used, is a prior art material which may be obtained from the Dycem Company, 83 Gilbane Street, Warwick, R.I. 02886 under the product name Protectamat Model CC02/06/1. The Protectamat is a contamination control mat laid on a floor over which people walk. To manufacture the polymer-cleaning element 16, as shown in FIG. 4a, the square cross-section elongated cleaning element pieces 16 are cut from the mat 18. This is also shown in a side view in FIG. 4b. Other materials may also be used having the characteristics previously described for the cleaning element.

The disclosed cleaning tool is useful on CCDs, films, camera mirrors, optics, and other sensitive surfaces. Minute particles such as small dust specs and/or hair can be safely removed from sensitive surfaces without damaging them. With just a general touch, the small particles or hairs are captured by the surface without leaving a residue. The removed or gathered contaminant or evidential material is easily cleaned or removed from the tool with water or other cleaning solution and when dry is ready for action again.

The disclosed tool saves time which would otherwise be spent retouching spots caused by contamination on the CCDs, transparencies, films and camera mirrors or the like. The cleaning tool disclosed is more effective then other methods that rely on solvents and non-woven materials.

Just a gentle touch of the tool adheres particles and/or hair without leaving a residue.

The cleaning element at the end of the tool provides a high adhesion surface that sticks to the contaminant particles and/or hair with considerably more cohesive force then the contaminated surface or surface from which evidential material is being gathered.

In one preferred embodiment, the tool is non-conductive and can be used on active CCDs allowing the technician to monitor the decontamination process.

Other uses of the cleaning tool are on disk drive heads, mirrors and lenses, UV windows, films and silicon wafers which are typically hard to clean surfaces.

When the tool is cleaned in water or a soap solution, for example, the adhesive qualities are not diminished.

The tool can be used on CCDs, optics, films, glass, SLR mirrors, transparencies, electro-optical devices, and other delicate surfaces.

The cleaning element does not have a separate chemical impregnation into the polymer, such as a glue or the like. The cleaning tool has no impregnation since the polymer material has inherent adhesion abilities for the minute particles and hairs.

FIG. 5 shows an embodiment of the tool particularly suited for evidence collecting, securing, identifying, and storing in police work. Reference numeral 19 generally shows the evidence gathering tool wherein the hollow plastic tube 14 having the polymer cleaning element 16 inserted at one end thereof has its other end received within an aperture 20A of a rubber stopper or plug 20 shaped as a cork which is press fit into the end of a relatively clear plastic storing or sample tube 21 in the shape of a test tube and which has at an open end a reinforcing collar 21A. In use, the evidence gathering tool is employed by pulling the end of the stopper 20 free from the end of the storing tube 21 and then dabbing the cleaning element 16 at a surface on which evidentiary materials to be collected are residing. The cleaning element 16 will adhere to not only small particles such as dust but also fibers, hairs, and even liquids. Thereafter, the gathered evidence is protected by reinserting the tool back into the storing tube 21 by press fitting the stopper 20 in the end of the storing tube 21. The gathered evidence is thus secured and protected. The side of the substantially clear plastic storing tube 21 can be used for marking or labeling of the collected specimen such as by a felt tip marker which can apply identification markings directly on the outer face of the storing tube 21, or by providing a label which is adhered to the sidewall of the storing tube 21. The tube 21 may also be constructed of glass in lieu of plastic.

Thus, the cleaning element 16 on the plastic tube 14 functions as a contaminant-free sampling tool.

The plastic storing tube 21 is preferably of about 150 mm in diameter, but can have a diameter ranging from 75 mm to 200 mm, for example.

Preferably, the storing tube 21 is constructed of polypropylene.

The evidence grabbing tool disclosed can be a single use tool.

While preferred embodiments have been illustrated and described in detail in the drawings and foregoing description, the same is to be considered as illustrative and not restrictive in character, it being understood that only the preferred embodiments have been shown and described and that all changes and modifications that come within the spirit of the invention both now or in the future are desired to be protected.

I claim as my invention:

1. A hand-held cleaning tool, comprising:

a flexible elongated member having at one end a polymer cleaning element and a gripping portion at the other end, the polymer cleaning element being non-abrasive with inherent adhesion for particles and hair, no aqueous solubility, non-corrosive, no particulate emission, and no separate chemical impregnation into the polymer element so that no residue is deposited by the tool when used; and the elongated member comprising a tube wherein the cleaning element has a substantially square cross-section with a first portion of the cleaning element being inserted into the tube in press-fit fashion and a remaining second portion outside the tube, corners of the inserted first portion of the cleaning element being compressed by the tube.

2. The tool of claim 1 wherein the polymer element comprises a piece cut from a contamination control mat.

3. The tool according to claim 1 wherein the tube comprises plastic.

4. The tool according to claim 1 wherein the flexible elongate member comprises a hollow plastic straw-like tube having a diameter of from $1/16''$ to $1/2''$.

5. The tool according to claim 4 wherein the tube has a diameter of from $1/16''$ to $1/8''$.

6. The tool according to claim 4 wherein the cleaning element has a length of approximately $1/2''$ inch or less and a cross-section of about $1/2''$ or less.

7. The tool according to claim 1 wherein the cleaning element comprises a polymer selected so that it will not damage a face of a charged coupled device (CCD) in an imaging device.

8. The tool according to claim 1 wherein the cleaning element is non-conductive.

9. The tool according to claim 1 wherein the gripping portion comprises a finger grip.

10. The tool according to claim 1 wherein the gripping portion comprises a stopper having an aperture for receiving the other end of the elongated member, the stopper being designed to be press fit into a storing tube for storing the tool when the tool is not in use and for storing a collected material.

11. A method for cleaning a surface, comprising the steps of:

providing a polymer cleaning element having a substantially square cross-section and which is non-abrasive with inherent adhesion for small particles and hair, no aqueous solubility, non-corrosive, without particulate emission, and without a separate chemical impregnation into the polymer;

providing an elongated member as a flexible tube, inserting a portion of the polymer cleaning element in press-fit fashion into one end of the tube and providing a gripping portion at an opposite end of the tube, corners of the inserted portion of the cleaning element being compressed by the tube; and holding the gripping portion of the elongated member with a user's fingers and lightly touching the cleaning element to the surface to pick up contaminate materials from the surface but without damaging the surface and without depositing a residue on the surface.

12. A method according to claim 11 wherein the surface comprises at least one of a CCD surface, an optics surface, a film surface, a glass surface, an SLR mirror surface, a transparency surface, and an electro-optical device surface.

13. A method according to claim 11 including the step of removing contaminate materials from the cleaning element by washing with water.

14. The method according to claim 11 wherein the polymer cleaning element comprises a piece cut from a contamination control mat.

15. The method of claim 11 including providing a storing tube, providing said gripping portion as a stopper inserted at one end of the storing tube, initially storing the elongated member with the cleaning element in the storing tube by press fitting the stopper into said one end of the storing tube, and then for collecting at least one of particles and hair, gripping the stopper to pull the elongated member free from the tube, dabbing the cleaning element to a surface to collect at least one of particles and hair, and then reinserting the stopper in said one end of the storing tube with the cleaning element inside the tube to store at least one of the collected particles and hair.

16. The method according to claim 15 including the step of providing the storing tube substantially clear and in a shape of a test tube.

17. The method according to claim 15 including the step of providing the storing tube substantially clear and identifying at least one of collected particles and hair by at least one of a writing or a label on a side of the storing tube.

* * * * *